US008388692B2

(12) United States Patent
Nakamura et al.

(10) Patent No.: US 8,388,692 B2
(45) Date of Patent: Mar. 5, 2013

(54) THIN FILM MULTILOCULAR STRUCTURE MADE OF COLLAGEN, MEMBER FOR TISSUE REGENERATION CONTAINING THE SAME, AND METHOD FOR PRODUCING THE SAME

(75) Inventors: Tatsuo Nakamura, Kyoto (JP); Yuji Inada, Kyoto (JP); Keiji Shigeno, Kyoto (JP)

(73) Assignee: Kyoto University, Kyoto (JP)

( * ) Notice: Subject to any disclaimer, the term of this patent is extended or adjusted under 35 U.S.C. 154(b) by 926 days.

(21) Appl. No.: 12/308,854

(22) PCT Filed: Jun. 29, 2007

(86) PCT No.: PCT/JP2007/063516
§ 371 (c)(1),
(2), (4) Date: Mar. 20, 2009

(87) PCT Pub. No.: WO2008/001952
PCT Pub. Date: Jan. 3, 2008

(65) Prior Publication Data
US 2009/0280161 A1    Nov. 12, 2009

(30) Foreign Application Priority Data

Jun. 30, 2006 (JP) .............................. P 2006-180802

(51) Int. Cl.
*A61F 2/02* (2006.01)
(52) U.S. Cl. .................................................. 623/23.72
(58) Field of Classification Search ................ 623/1.38, 623/1.44, 1.46, 1.47, 23.72, 23.74
See application file for complete search history.

(56) References Cited

U.S. PATENT DOCUMENTS 3,833,002 A    9/1974  Palma
(Continued)

FOREIGN PATENT DOCUMENTS

| JP | 64-004629 | 1/1989 |
| JP | 11-511039 | 9/1999 |

(Continued)

OTHER PUBLICATIONS

International Search Report issued Aug. 23, 2007 in the International (PCT) Application of which the present application is the U.S. National Stage.

(Continued)

*Primary Examiner* — Ryan Severson
(74) *Attorney, Agent, or Firm* — Wenderoth, Lind & Ponack, L.L.P.

(57) ABSTRACT

A new structure made of collagen for improving promotion of nerve tissue regeneration, curing and regeneration of a defective part of a soft biological tissue and so on without using laminin or nerve growth factor (NGF), and a member for tissue regeneration including the same. The structure made of collagen has a thin film multilocular formation and is therefore a new structure different from a colloid form, a gel form, and a fiber form. When the new structure made of collagen is used as a member for tissue regeneration, surprisingly, promotion of regeneration, shortening of a treatment period, functional recovery, or the like of bodily tissue such as nerve tissue, subdermal tissue, submucosal tissue, membranous tissue, fat tissue, muscle tissue, skin tissue, and gingival tissue can be improved. When the structure is used in a patient having neuropathic pain, the member has an effect on the disappearance of the pain.

14 Claims, 10 Drawing Sheets

U.S. PATENT DOCUMENTS

| | | | |
|---|---|---|---|
| 4,412,947 | A | 11/1983 | Cioca |
| 4,662,884 | A | 5/1987 | Stensaas |
| 6,090,117 | A | 7/2000 | Shimizu |
| 6,228,111 | B1 | 5/2001 | Tormala et al. |
| 2002/0052649 | A1* | 5/2002 | Greenhalgh ............... 623/1.35 |
| 2002/0086423 | A1* | 7/2002 | Takezawa et al. ........... 435/397 |
| 2006/0100647 | A1 | 5/2006 | Doi et al. |

FOREIGN PATENT DOCUMENTS

| | | |
|---|---|---|
| JP | 2001-340446 | 12/2001 |
| JP | 2003-19196 | 1/2003 |
| JP | 2004-208808 | 7/2004 |
| JP | 2004-254759 | 9/2004 |
| JP | 2005-143979 | 6/2005 |
| WO | 98/22155 | 5/1998 |

OTHER PUBLICATIONS

Y. Inada et al., "Surgical relief of causalgia with an artificial nerve guide tube: Successful surgical treatment of causalgia (Complex regional Pain Syndrome Type II) by in situ tissue engineering with a polyglycolic acid-collagen tube", Pain, vol. 117, No. 3, pp. 251-258, 2005.

T. Ito et al., "Biodegradation of Polyglycolic Acid-Collagen Composite Tubes for Nerve Guide in the Peritoneal Cavity", ASAIO Journal, vol. 49, No. 4, pp. 417-421, 2003.

C. A. Heath et al., "The development of bioartificial nerve grafts for peripheral-nerve regeneration", Trends in Biotechnology, Vo. 16, No. 4, pp. 163-168, 1998.

S. Ichihara et al., "Kyori no aru Shinkei Kesson ni Taisuru Atarashii Shinkei Tube no Kaihatsu", The Journal of Japanese Orthopaedic Association, vol. 81, No. 4, p. S457, Apr. 2007.

A. G. Mikos et al., "Preparation of poly(glycolic acid) bonded fiber structures for cell attachment and transplantation", Journal of Biomedical Materials Research, vol. 27, No. pp. 183-189, 1993.

Lee, D. et al., Nerve regeneration with the use of a poly(L-lactide-co-glycolic acid)-coated collagen tube filled with collagen gel, *Journal of Cranio-Maxillofacial Surgery*, vol. 34 (2006), pp. 50-56.

English translation of Ichiahara, S. et al., Development of a Novel Nerve Tube for Long Defective Part of Nerve, *The Journal of Japanese Orthopaedic Association*, vol. 81, No. 4 (2007), p. S457.

Supplementary European Search Report dated Mar. 25, 2010 in Application No. EP 07 79 0457.

Hiroki Ueda et al., "Use of collagen sponge incorporating transforming growth factor-$\beta1$ to promote bone repair in skull defects in rabbits", Biomaterials, 2002, vol. 23, pp. 1003-1010.

Toshinari Toba et al., "Peripheral Nerve Regeneration Using a Polyglycolic Acid (PGA)-Collagen Nerve Conduit Filled with Collagen Sponge: Experimental Research and Human Application", Connective Tissue, 2003, vol. 35, pp. 45-52.

\* cited by examiner

From Part in which Nerve is regenerated, Tube is Degraded and Absorbed

THIN FILM MULTILOCULAR STRUCTURE MADE OF COLLAGEN, MEMBER FOR TISSUE REGENERATION CONTAINING THE SAME, AND METHOD FOR PRODUCING THE SAME

This application is a U.S. national stage of international Application No. PCT/JP2007/063516 filed Jun. 29, 2007.

TECHNICAL FIELD

The present invention relates to a thin film multilocular structure made of collagen, a member for tissue regeneration containing the same, various supports used for the member for tissue regeneration, and a method for producing the same. More particularly, the present invention relates to a member for regenerating a nerve tissue containing the thin film multilocular structure made of collagen, and a method for producing the same including freeze-drying a collagen solution.

BACKGROUND ART

In United States, a tube for connecting nerve tissues by using collagen is already commercially available as NeuraGen nerve guide (trade name) from Integra NeuroCare LLC, USA, and a tube for connecting nerve tissues by using polyglycolic acid (PGA) is commercially available as GEM Neurotube (trade name) from Synovis Micro companies Alliance, USA. These neuron connection tubes are hollow tubes inside which nothing is filled, and can be used for regenerating a peripheral sensory nerve in which a length of a defective part of the nerve is up to 2 cm. When the hollow tubes are implanted in the defective parts of the nerves, nerve fibers are regenerated in the defective parts.

However, when the defective part is longer than 2 cm, the use of the nerve connection tube is limited. This is because in the hollow tube, the potential for promoting the regeneration of nerve is poor and the decomposition thereof is rapid and therefore there are such problems as the hollow tube cannot be used for longer defective parts. Furthermore, in the hollow tubes that are commercially available in United States, there is a problem that if there is an aperture difference between the aperture of the end of the hollow tube and the aperture of the end of the neuron, a gap is generated between both the apertures and therefore surrounding tissue inhibiting the progress of the nerve tissue invades the gap and inhibits the progress of nerve generation. Moreover, there is a problem that when the defective part of the peripheral nerve branches, one hollow tube cannot be used and the implanting operation is troublesome. There is a further problem that the sustainability of the lumen of the hollow tube is insufficient. Therefore a long defective part cannot be repaired, the nerve cannot extend and regeneration stops. Moreover, there is a problem depending on the region used, both ends cannot be inserted in the nerve tube.

Recently, an artificial nerve tube containing sponge-like or gel-like collagen in a tube has been made of a biodegradable absorbable material (such as polylactic acid and polyglycolic acid). For example, Patent Document 1 (WO 98/22155) discloses an artificial nerve tube containing a gel consisting of collagen and laminin in a tube made of a biodegradable absorbable material (such as polylactic acid and polyglycolic acid).

Patent Document 2 (Japanese Unexamined Patent Publication (Kokai) No. 2003-019196) discloses a tube for regenerating nerve which is made of an outer layer of a bioabsorbable material (such as polylactic acid) and an inner layer made of a sponge-like substance of collagen and a lactic acid/$\epsilon$-caprolacton copolymer.

Patent Document 3 (Japanese Unexamined Patent Publication (Kokai) No. 2004-208808) discloses an inductive tube for nerve regeneration containing a sponge-like collagen inside a tubular body made of a biodegradable material or bioabsorbable material (such as protein, polysaccharide, polylactic acid, and polyglycolic acid).

Patent Document 4 (Japanese Unexamined Patent Publication (Kokai) No. 2005-143979) discloses a nerve-regenerating tube in which fiber-like synthetic bioabsorbable polymer (such as polylactic acid and polyglycolic acid) coated with collagen is filled inside a tubular body made of bioabsorbable material polymer (such as polylactic acid and polyglycolic acid).

Non-Patent Document 1 (Lee D Y et al, Journal of Cranio-Maxillofacial Surgery (2006) 34, 50-56, "Nerve regeneration with the use of a poly-L-lactide-co-glycolic acid-coated collagen tube filled with collagen gel") discloses an artificial nerve tube containing a gel-like collagen in a tubular body made of polylactic acid and polyglycolic acid.

In Patent Documents 1 to 4 and Non-Patent Document 1, collagen having a sponge-like, gel-like, or fiber-like structure is included inside a biodegradable material of a tubular body, and therefore, compared to a hollowing body containing no collagen, the collagen serves as a so-called scaffold for nerve regeneration, and thereby, there is an advantage that the nerve regeneration is more promoted.

However, additional there is an increasing need for not only for promotion of nerve tissue regeneration and assisting tissue restoration, but also for improvement of clinical performance by accelerating recovery of physiological functions of nerve tissue. Moreover, there are such problems that clinical application is not possible because laminin which is a physiologically active substance the security of which is yet to be established is used, that the tubes cannot be used for longer defective parts because the decomposition thereof is rapid, that a gap is generated if there is an aperture difference between the artificial nerve and cut end of the nerve, that the tubes cannot be used if a branch exists, that the sustainability of the lumen is also insufficient and that occasionally both ends cannot be inserted into the neural tube.

DISCLOSURE OF THE INVENTION

The present invention has been accomplished to solve the above-mentioned problems, and an object of the present invention is to provide a new structure made of collagen for improving promotion of nerve tissue regeneration, curing and regeneration of a defective part of a soft biological tissue, and so forth without using laminin or nerve growth factor (NGF).

Moreover, an object of the present invention is to provide a member for tissue regeneration for ameliorating or preferably substantially eliminating at least one of such problems that the tubes cannot be used for longer defective parts because the decomposition thereof is rapid, that a gap is generated if there is an aperture difference between the artificial nerve and cut end of the nerve, that the tubes cannot be used if a branch exists, that the sustainability of the lumen is also insufficient and that occasionally both ends cannot be inserted into the neural tube.

Another object of the present invention is to provide a support used for such a member for tissue regeneration and a method for producing the same.

Furthermore, still another object of the present invention is to provide a new structure made of collagen, a member for tissue regeneration containing the same, a support used for the member for tissue regeneration, and a method for producing the above-described member for tissue regeneration.

The present inventors have performed intensive studies for solving such problems, and as a result, have made the surprising discovery that collagen having a specific form is useful for improving promotion of regeneration, shortening of curing period, functional recovery, or the like of bodily tissues such as nerve tissue, subdermal tissue, submucosal tissue, membranous tissue, fat tissue, muscle tissue, skin tissue, and gingival tissue and the above-described problems can be solved by using collagen having such a specific form, and thus the present invention has been accomplished.

That is, in one aspect, the present invention provides a new structure made of collagen and the structure is a thin film multilocular structure made of collagen.

In another aspect of the present invention, a member for tissue regeneration containing the above-described thin-film multilocular structure is provided.

In one embodiment of the present invention, a member for tissue regeneration further including a biodegradable support is provided.

In a preferred embodiment of the present invention, a member for tissue regeneration is provided having the above-described thin film multilocular structure inside a tubular biodegradable support.

Furthermore, the present inventors have performed intensive studies, and as a result, have found that by using a biodegradable support having a U-shaped or C-shaped section (namely, overall a trough shape), a tubular structure is not required for regeneration of nerve tissue on a fascia or on a coat of organ or the like and suture operation in implanting is facilitated and operating times can be shortened.

That is, in another preferred embodiment of the present invention, a member for tissue regeneration having the above-described thin film multilocular structure inside a biodegradable support having a trough-shaped form whose section has a U-shape or C-shape is provided.

Moreover, the present inventors have performed intensive studies, and as a result, have found that by using a biodegradable support having a branch, if there is a branch in the defective part of the peripheral nerve, the one hollow tube is sufficient for the defective part.

That is, in a further embodiment of the present invention, the above-described member for tissue regeneration in which the biodegradable support has a branch is provided.

Furthermore, the present inventors have performed intensive studies, and as a result, have found that by using a tubular or trough-shaped support having an aperture difference between the aperture of one end of the biodegradable support and the aperture of the other end thereof, a gap between the member for tissue regeneration in which the support is used and the nerve tissue is not generated.

That is, in a further embodiment of the present invention, the above-described member for tissue regeneration having an aperture difference between the aperture of one end of the biodegradable support and the aperture of the other end thereof is provided.

Furthermore, the present inventors have performed intensive studies, and as a result, have found that by using a biodegradable support in which decomposition rate of the biodegradable support having a tubular or trough-shaped form is changed such that the decomposition rate of the ends is higher than that of the central portion, the outer wall around the part in which the nerve tissue has been regenerated is sequentially degraded and therefore nutrition enters into the regenerated nerve from the surroundings and removal of the member by secondary surgery is not required.

That is, in a further preferred embodiment of the present invention, the above-described member for tissue regeneration including the biodegradable support in which degradation rate of the biodegradable support having a tubular or trough-shaped form is changed such that the decomposition rate of the ends is higher than that of the central portion is provided.

Moreover, the present inventors have performed intensive studies, and as a result have found that by using a biodegradable support in which a structure having a hollow interior is maintained by mixing a raw material which is slowly degraded in vivo with a raw material which is rapidly degraded in vivo to delay the degradation thereof in vivo, the degradation rate of the biodegradable support becomes slow (or inactive) and the structure having a hollow inside is maintained for a long period if the defective part of tissue is long.

That is, in a preferred embodiment of the present invention, the member for tissue regeneration including the biodegradable support in which a structure having a hollow interior with the tubular or trough-shaped is maintained by mixing a raw material degraded slowly in vivo with a raw material degraded rapidly in vivo to delay the degradation thereof in vivo is provided.

It is more preferable that the biodegradable support in which the structure having a hollow interior is maintained by delaying the degradation in vivo is used in combination with the above-described biodegradable support whose degradation rate is higher as being nearer to both ends from the central portion. That is, the member for tissue regeneration including the biodegradable support in which the degradable rate of the biodegradable support is higher as being nearer both end portions from the central portion and in which the structure having a hollow interior is maintained by mixing the raw material which is slowly degraded in vivo with the raw material which is rapidly degraded in vivo to delay the degradation in vivo is more preferable. Thereby, the member for tissue regeneration including the biodegradable support in which the structure having a hollow interior is maintained in the central portion with degrading the member for tissue regeneration from the ends in vivo is provided.

That is, in a further preferred embodiment of the present invention, the above-described member for tissue regeneration in which the degradation rate of the biodegradable support having a tubular or trough-shaped form is changed such that the decomposition rate of the ends is higher than that of the central portion in vivo and in which the structure having the hollow interior inside of a tubular or trough-shaped form is maintained by mixing the raw material which is slowly degraded in vivo with the raw material which is rapidly degraded in vivo to delay the degradation in vivo is provided.

The member for tissue regeneration according to the present invention is not particularly limited with respect to the tissue to be used as long as the member can be used for bodily tissue and can regenerate the tissue. Use for regenerating nerve tissue is more preferable.

In another aspect of the present invention, a method for producing the above-described thin film multilocular structure including freeze-drying a collagen solution is provided.

In another preferable aspect of the present invention, the method for producing the member for tissue regeneration includes immersing the biodegradable support supporting the above-described thin film multilocular structure in the collagen solution and then freeze-drying the collagen solution.

The structure made of collagen according to the present invention has a thin film multilocular formation (constitution or form) and therefore a new structure different from a colloid form, a gel form, and a fiber form. Therefore, when the new structure made of collagen according to the present invention is used as a member for tissue regeneration, surprisingly, promotion of regeneration, shortening of a treatment period, functional recovery, or the like of bodily tissue such as nerve tissue, subdermal tissue, submucosal tissue, membranous tissue, fat tissue, muscle tissue, skin tissue, and gingival tissue can be improved.

Furthermore, when the above-described member for tissue regeneration includes the biodegradable support, the tissue to be regenerated can be protected.

When the member for tissue regeneration according to the present invention has the above-described thin film multilocular structure inside the tubular biodegradable support, a thready and long linear tissue can be regenerated more advantageously.

When the member for tissue regeneration according to the present invention has the above-described thin film multilocular structure inside the biodegradable support having a trough-shape whose section has a U-shape or C-shape, regeneration of tissue existing on a flat part such as on a fascia or on a fascia of an organ can be more easily performed.

When the biodegradable support has a branch in the member for tissue regeneration according to the present invention, a tissue having a branch can be regenerated by one member for tissue regeneration.

When there is the aperture difference between the aperture of one end of the biodegradable support and the aperture of the other end thereof in the member for tissue regeneration according to the present invention, the generation of the aperture gap between the aperture of the member for tissue regeneration and the aperture of the tissue of the defective part can be avoided.

When the member for tissue regeneration according to the present invention includes the biodegradable support having a tubular or trough-shaped form in which degradation rate of the biodegradable support is changed such that the decomposition rate of the ends is higher than that of the central portion, regeneration of the tissue is improved and the member is not required to be removed by a secondary operation.

It is preferable for regenerating a tissue having a long defective part that the member for tissue regeneration according to the present invention includes the biodegradable support in which the structure having a hollow interior inside a tubular or trough-shaped form is maintained by mixing a raw material which is slowly degraded in vivo with a raw material which is rapidly degraded in vivo to delay the degradation in vivo because the structure having a hollow interior in vivo is maintained for a long period.

The member for tissue regeneration according to the present invention can be suitably used for nerve tissue, subdermal tissue, submucosal tissue, membranous tissue, fat tissue, muscle tissue, skin tissue, gingival tissue, and so forth, and in particular, it is preferable to use the member for regeneration of neural tissue.

Furthermore, according to the method for producing the above-described new structure of collagen according to the present invention, the structure can be produced by freeze-drying a collagen solution and therefore the new structure of collagen can be produced very simply and easily.

Moreover, in the method for producing the new member for tissue regeneration according to the present invention, the production can be performed very simply and easily by freeze-drying a collagen solution in the state that the above-described support is immersed in a collagen solution.

BEST MODE FOR CARRYING OUT THE INVENTION

Hereinafter, the present invention will be explained more specifically and in detail with reference to the appended drawings. These descriptions are for merely explaining the present invention and it should be understood that the descriptions have no intention of limiting the present invention.

The present invention provides a structure made of collagen and this is a thin film multilocular structure.

In the present invention, "collagen" is a generally called "collagen" and is not particularly limited as long as "thin film multilocular structure" desired by the present invention can be obtained. Such a "collagen" includes collagens derived from bovine, pig, and human, but atelocollagen having little antigenicity is particularly preferable.

Figure 1A:
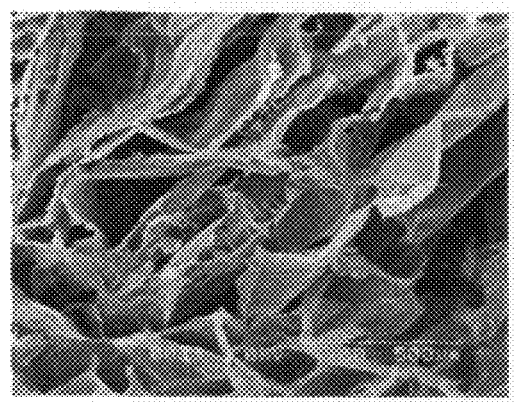
FIG. 1(a) shows a scanning electron micrograph at a low magnification (about ×80) of the thin film multilocular structure made of collagen according to the present invention.
Figure 1B:
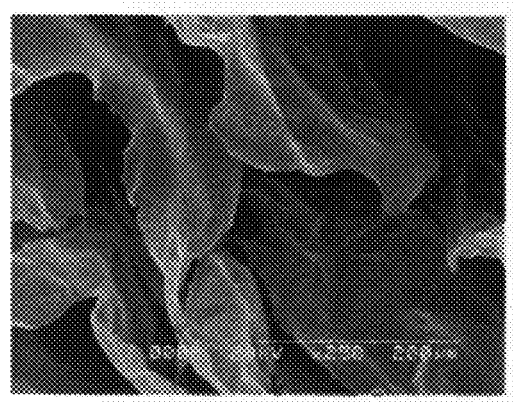
FIG. 1(b) shows a scanning electron micrograph at a middle magnification (about ×250) of the thin film multilocular structure made of collagen according to the present invention.
Figure 1C:
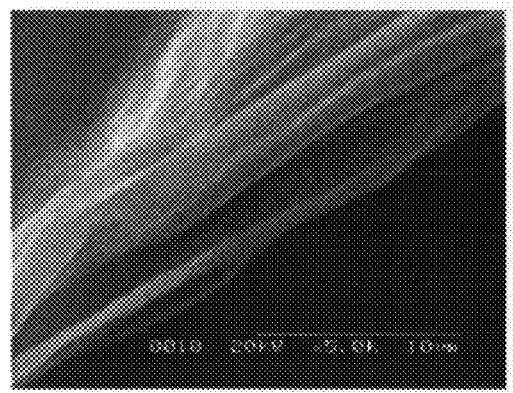
FIG. 1(c) shows a scanning electron micrograph at a high magnification (about ×5,000) of the thin film multilocular structure made of collagen according to the present invention.
Figure 1D:
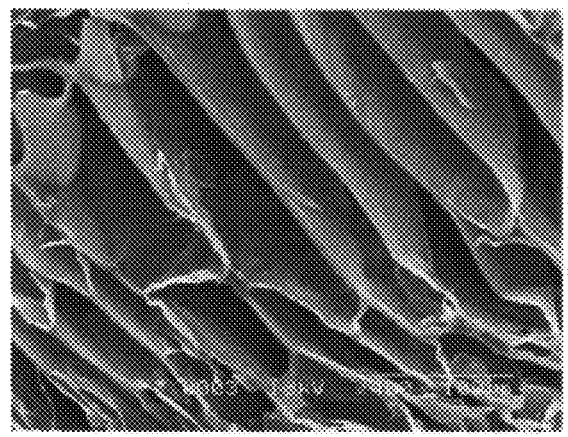
FIG. 1(d) shows a scanning electron micrograph at a middle magnification (about ×400) of the thin film multilocular structure made of collagen according to the present invention.
Figure 1E:
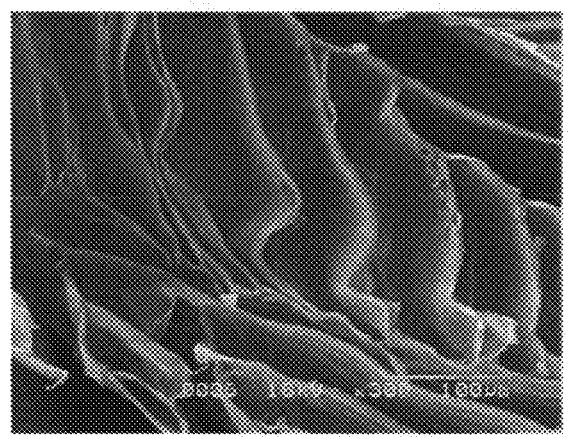
FIG. 1(e) shows a scanning electron micrograph at a middle magnification (about ×300) of the thin film multilocular structure made of collagen according to the present invention.

In the present invention, "thin film multilocular structure" is substantially composed of a thin film-shaped collagen and has a structure including many loculi (or chambers) between the thin films. FIGS. 1(a) to 1(e) show scanning electron micrographs of the thin film multilocular structure made of collagen according to the present invention. For FIGS. 1(a) to 1(c), the acceleration voltage of scanning electron microscopy is 20 kV. FIG. 1(a) shows an image at a low magnification (about ×80), and FIG. 1(b) shows an image at a middle magnification (about ×250), and FIG. 1(c) shows an image at a high magnification (about ×5,000). Moreover, for FIGS. 1(d) to 1(e), the acceleration voltage of scanning electron microscopy is 18 kV. FIG. 1(d) shows an image at a middle magnification (about ×400), and FIG. 1(e) shows an image at a middle magnification (about ×300). The "thin film multilocular structure" made of collagen is made of many thin films whose surfaces are flat such as "pie of a western confectionery", and it is understood that fiber-formed collagen is not included.

The film thickness of the "thin film" is preferably 0.01 to 200 μm, and more preferably 0.1 to 50 μm, and particularly preferably 0.5 to 5 μm. Furthermore, intervals of films of the "thin film multilocular structure" are, for example, about 50 μm to about 3 mm, and preferably 300 μm to 2,000 μm. The bunchy space composed by the thin films may be continuous or closed.

Conventionally, as the "structure made of collagen", sponge-formed structure, gel-formed structure, and fiber-formed structure are known, but the above-described "thin film multilocular structure" is not known at all and first has been found by the present inventors.

Examples of the sponge-formed structure and the thready fiber-formed structure of collagen that are conventionally known are shown in FIGS. 11 to 14. The acceleration voltage of scanning electron microscopy of FIGS. 11(a) to 11(c) is 20 kV, and the acceleration voltage of FIG. 12(a) is 8 kV and the acceleration voltage of FIG. 12(b) is 9 kV and the acceleration voltage of FIG. 14(b) is 18 kV, and the acceleration voltage of FIGS. 13(a) to 13(b) and 14(a) is 25 kV.

Figure 11A:
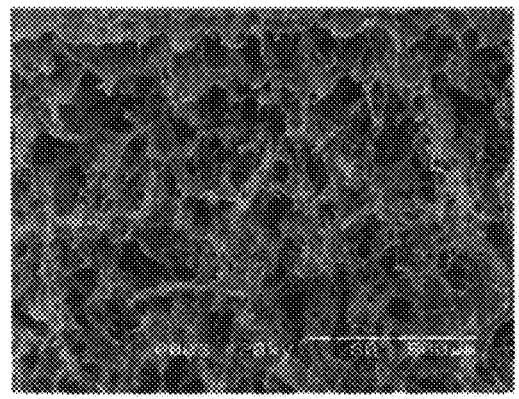
FIG. 11(a) shows a scanning electron micrograph at a low magnification (about ×80) of one example of sponge-formed collagen.
Figure 11B:
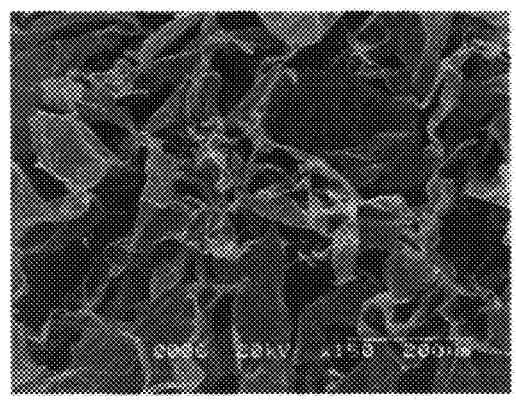
FIG. 11(b) shows a scanning electron micrograph at a middle magnification (about ×150) of one example of sponge-formed collagen.
Figure 11C:
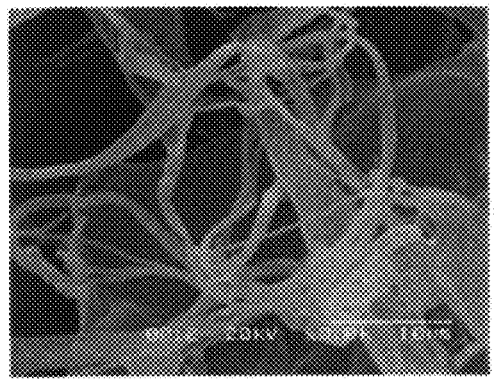
FIG. 11(c) shows a scanning electron micrograph at a high magnification (about ×3,000) of one example of sponge-formed collagen.

FIGS. 11(a) to 11(c) are scanning electron micrographs of the sponge-formed collagen that is being used clinically now as an artificial dermis (PELNAC (trade name), manufactured by Gunze Co., Ltd. and distributed by Johnson & Johnson Inc. FIG. 11(a) is an image at a low magnification (about ×80), and FIG. 11(b) is an image at a middle magnification (about ×150), and FIG. 11(c) is an image at a high magnification (about ×3,000).

Figure 12A:
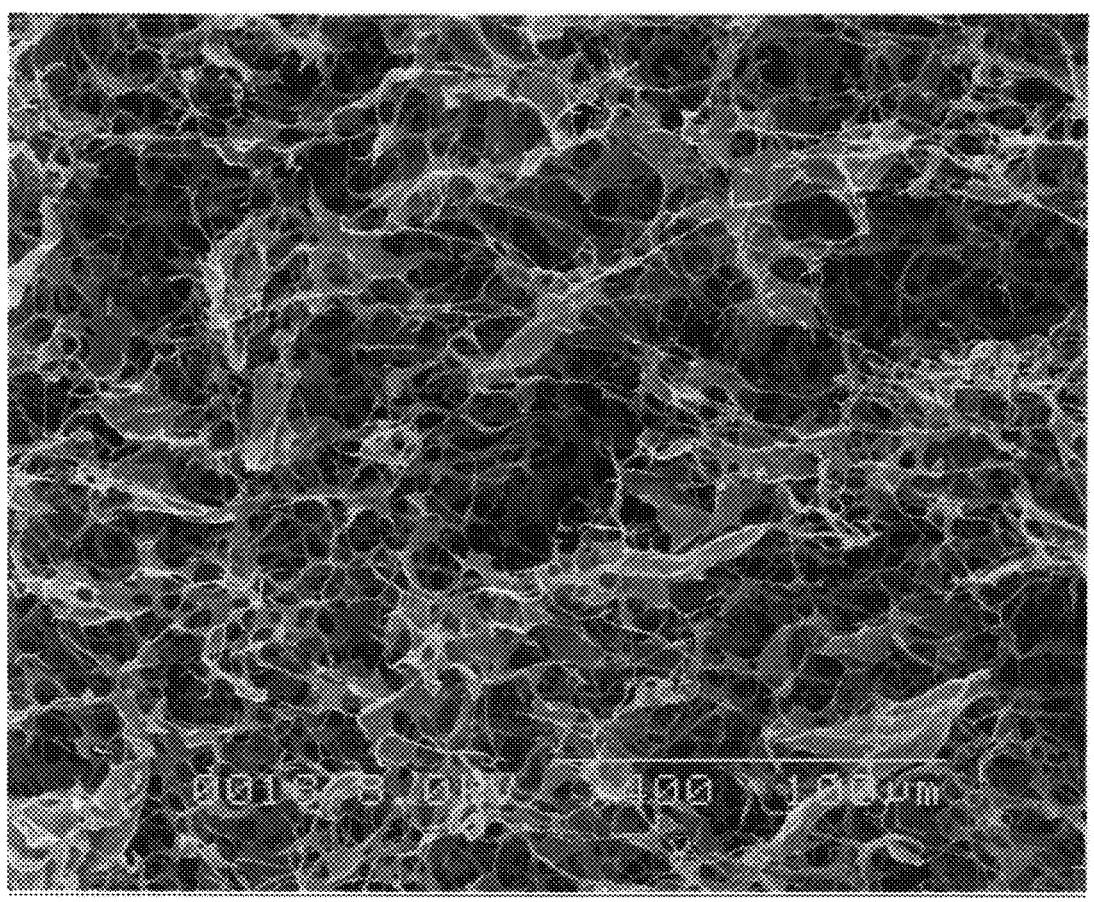
FIG. 12(a) shows a scanning electron micrograph at a middle magnification (about ×400) of one example of sponge-formed collagen.
Figure 12B:
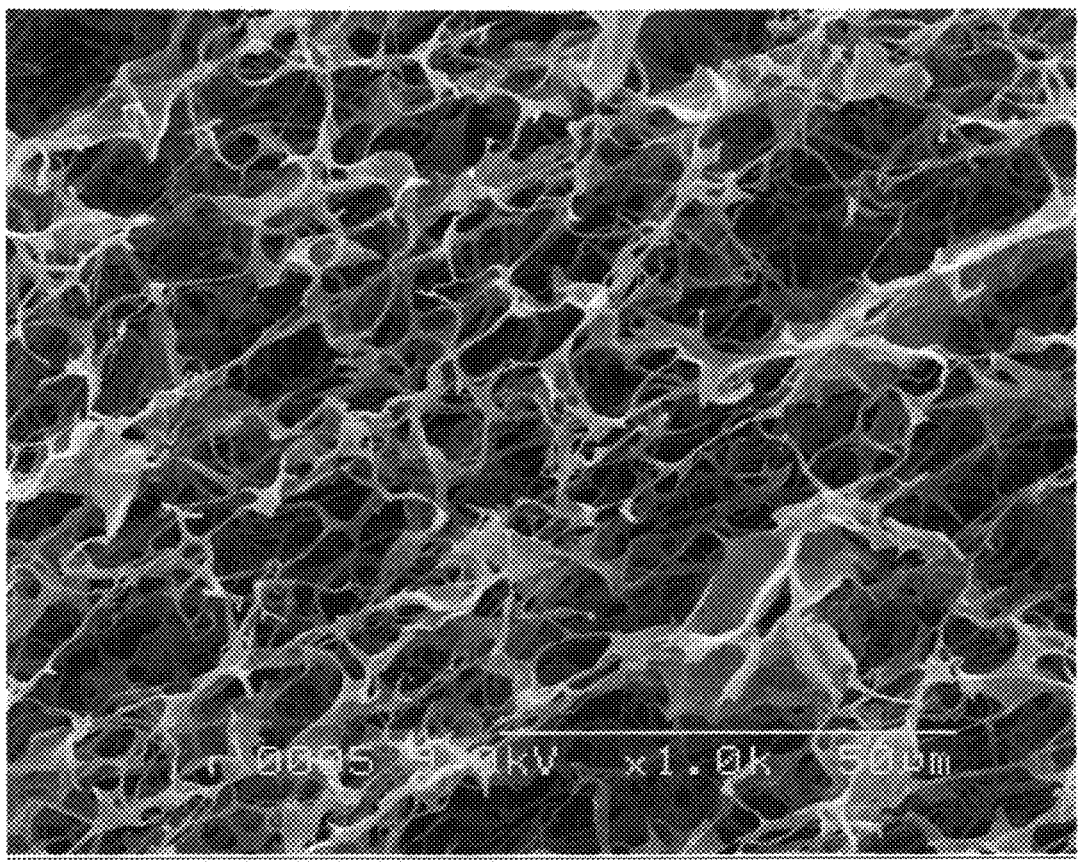
FIG. 12(b) shows a scanning electron micrograph at a high magnification (about ×1,000) of one example of sponge-formed collagen.

Furthermore, FIGS. 12(a) and 12(b) are scanning electron micrographs of sponge-formed collagen. FIG. 12(a) is an image at a middle magnification (about ×400), and FIG. 12(b) is an image at a high magnification (about ×1,000). The sponge-formed collagen was obtained as follows. Atelocollagen (NMP collagen PSN (trade name) manufactured by Nippon Meat Packers, Inc. derived from pig dermis) was mixed in water (pH=about 7.0) so as to be 1% by weight, and stirred for about 30 minutes at 12,000 revolutions per minute, and then injected into a frame, and frozen at −196° C., and dried for 24 to 48 hours at −80° C. by a freeze-drier to evaporate moisture, and then, subjected to a cross-linking treatment by heating for 24 hours at 140° C. under vacuum conditions, and thereby, a sponge-formed collagen was obtained.

It can be understood that the collagen has a sponge-formed hollow structure because of thready collagen fiber. Therefore, the basic unit composing the sponge-formed collagen is fiber.

Figure 13A:
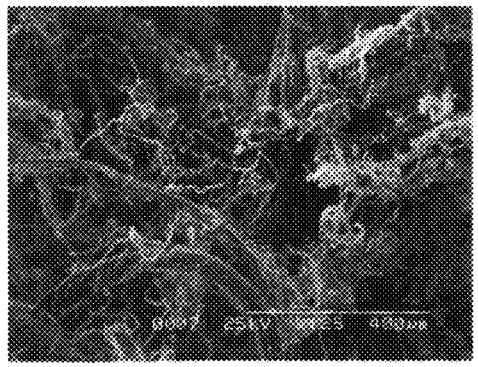
FIG. 13(a) shows a scanning electron micrograph at a middle magnification (about ×125) of one example of fine fiber collagen.
Figure 13B:
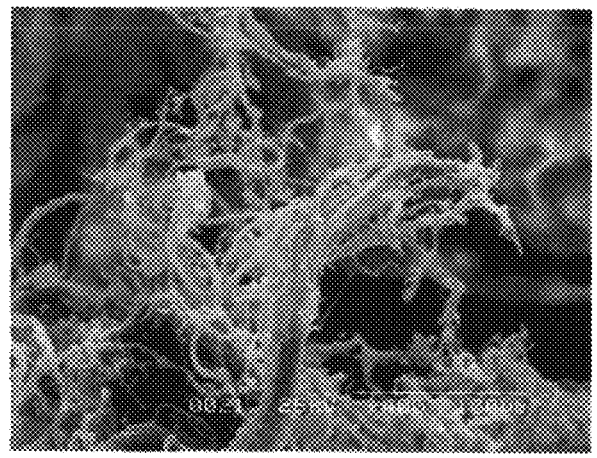
FIG. 13(b) shows a scanning electron micrograph at a middle magnification (about ×400) of one example of fine fiber collagen.

FIGS. 13(a) and 13(b) are scanning electron micrographs of commercially available fiber collagen as local hemostatic (Aviten (trade name) manufactured by Alcon-(Puerto Rico) Inc, Humacal, Puerto Rico, and imported and distributed by Zeria Pharmaceutical Co., Ltd.). FIG. 13(a) is an image at a middle magnification (about ×125), and FIG. 13(b) is an image at a middle magnification (about ×400).

Figure 14A:
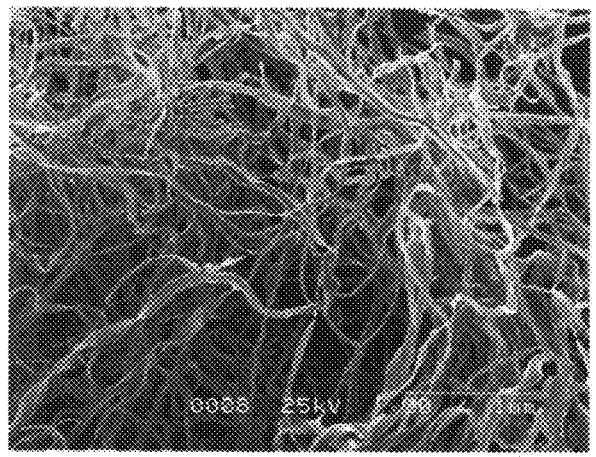
FIG. 14(a) shows a scanning electron micrograph at a low magnification (about ×30) of one example of fine fiber collagen.
Figure 14B:
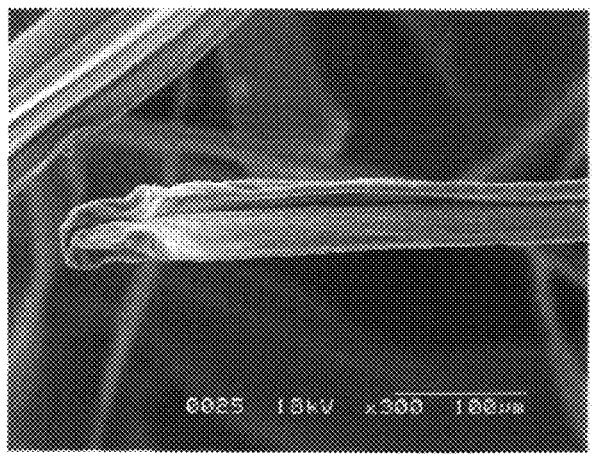
FIG. 14(b) shows a scanning electron micrograph at a middle magnification (about ×300) of one example of fine fiber collagen.

FIGS. 14(a) and 14(b) are scanning electron micrographs of commercially available fiber collagen as absorbable local hemostatic (Integran (trade name) manufactured by Koken Co., Ltd., and distributed by Nippon Zoki Pharmaceutical Co., Ltd.). FIG. 14(a) is an image at a low magnification (about ×30), and FIG. 14(b) is an image at a middle magnification (about ×300).

In both, fine collagen fiber forms a structure like nonwoven cloth. It can be understood that the structure is formed from collagen fiber bundle and straggling fiber thereof. The basic unit composing the fine fiber collagen is fiber.

When FIGS. 1(a) to 1(e), 11(a) to 14(b) are compared, it can be understood that the "thin film multilocular structure" made of collagen according to the present invention is obviously distinguished from gel-formed collagen and fiber-formed collagen.

The thin film multilocular structure made of collagen according to the present invention can be used for regenerating tissue. Here, the tissue is a bodily tissue of an animal such as human, rat, dog, cat, monkey, horse, cow, and sheep, and particularly, can be suitably used for the bodily tissue of human. The tissues from animals can includes nerve tissue, subdermal tissue, submucosal tissue, membranous tissue, fat tissue, muscle tissue, skin tissue, and gingival tissue, and in particular can be suitably used for nerve tissue. Therefore, the present invention provides the member for tissue regeneration including the thin film multilocular structure made of collagen. Here, as the bodily tissue, the following tissues can be exemplified:

nerve tissue (such as central nerve, peripheral nerve, ischiadic nerve, median nerve, facial nerve, cranial nerve, brachial plexus, ulnar nerve, radial nerve, femur nerve, ischiadic nerve, peroneal nerve, and sural nerve);
subdermal tissue;
submucosal tissue, oral submucosal tissue, digestive-tube submucosal tissue, genital submucosal tissue;
membranous tissue (such as cerebral dura mater, peritoneum, pleural membrane, fascia, membrane of organ);
fat tissue (such as so-called fat);
muscle tissue (such as so-called muscle);
skin tissue (such as so-called skin); gingival tissue (such as periodontal tissue, alveolar bone, dental alveolar tissue);
substantial organ (such as liver, kidney, lung, pancreas, thyroid gland); and
other (such as blood vessel, tendon, ligament, cartilage, and bone).

Furthermore, the present invention provides the member for tissue regeneration further including the biodegradable support. Here, "biodegradable support" has a property of being degraded in vivo and can form a backbone structure of the member for tissue regeneration, and is not particularly limited, as long as it is capable of adhering to and holding the thin film multilocular structure made of collagen and the member for tissue regeneration desired by the present invention can be obtained. Materials for producing such biodegradable support include polyglycolic acid (PGA), polylactic acid (PLA), copolymer of lactaid and glucorid (such as polyglactin 910), poly-ε-caprolacton, and copolymer of lactic acid and ε-caprolacton.

Figure 2A:
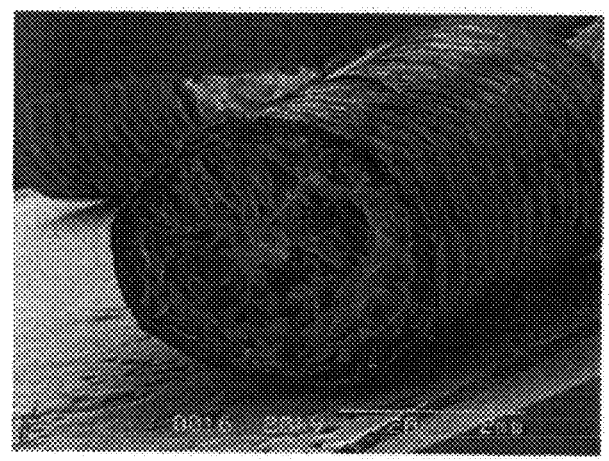
FIG. 2(a) shows a scanning electron micrograph of a cross section (about ×20) of one example of the tubular member for tissue regeneration including the thin film multilocular structure made of collagen according to the present invention.
Figure 2B:
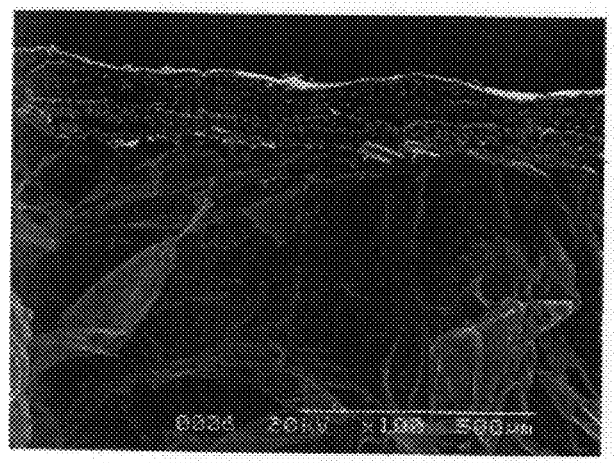
FIG. 2(b) shows a scanning electron micrograph of a longitudinal section (about ×100) of one example of the tubular member for tissue regeneration including the thin film multilocular structure made of collagen according to the present invention.

In FIGS. 2(a) and 2(b), scanning electron micrographs of the cross section (about ×20) and longitudinal sections (about ×100) of one example of the member for tissue regeneration including the thin film multilocular structure made of collagen according to the present invention are shown. The acceleration voltage of the scanning electron microscope is 20 kV. This is also one example of the member for tissue regeneration having the above-described thin film multilocular structure made of collagen inside of a tubular biodegradable support. By using the tubular biodegradable support, the member for tissue regeneration having a tubular form can be obtained. In the case of FIGS. 2(a) and 2(b), it is understood that inside the tubular biodegradable support made of PGA, the structure having many loculi (or chambers) is formed by a thin film made of collagen. As described above, it is more preferable that the thin film multilocular structure made of collagen is included inside the tubular biodegradable support, and in this case, the member can be suitably used for regeneration of nerve tissue, subdermal tissue, submucosal tissue, membranous tissue, fat tissue, muscle tissue, skin tissue, and gingival tissue.

Conventionally, the nerve connection tube having a tubular form has been used. The present inventors have found that the members for tissue regeneration having various forms can be used according to the tissue and that such members for tissue regeneration having various forms have the respective characteristic advantages. Such forms includes a form having a U-shaped or C-shaped section (namely, an overall trough-shaped form), a plate form, a branching form, and a form having aperture difference between the aperture of one end and the aperture of the other end (tapering form).

Figure 3:
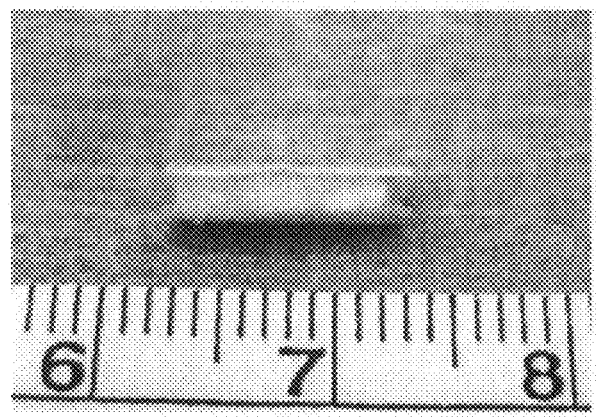
FIG. 3 shows one example of the member for tissue regeneration in a trough-shaped form having a U-shaped section.
Figure 4:
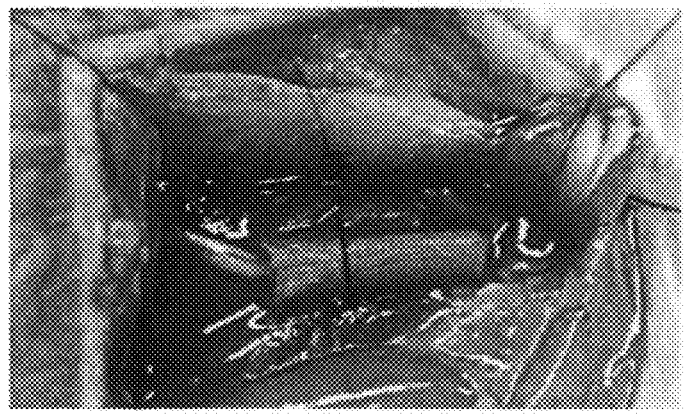
FIG. 4 shows one example of connecting the defective part (or defect) of 1 cm of ischiatic nerve of a rat by using the member for tissue regeneration having a U-shaped cross-section.

When the biodegradable support having U-shaped or C-shaped section is used, the member for tissue regeneration having U-shaped or C-shaped section (namely, overall having a trough shape) can be obtained. FIG. 3 shows one example of such member for tissue regeneration having U-shaped or C-shaped section. FIG. 4 shows one example of connecting a 1 cm defective part of ischiadic rat nerve by using such members for tissue regeneration having U-shaped or C-shaped section. The members of FIGS. 3 and 4 both have all of the sections having overall a trough-shaped form. When the member for tissue regeneration having such a form is used, in the case that the tissue to be regenerated exists on a fascia or on a dermis of an organ, a suture operation can be performed more easily. In the current operative method, the nerve tube is implanted by microscope operation. However, it is preferable to use the present support because implanting thereof can be easily and safely performed under an endoscope even deep inside a body in which microsurgery is impossible and further the time of the operation can be shortened. It is preferable that inside such a biodegradable support having U-shaped or C-shaped section, the thin film multilocular structure made of collagen according to the present invention is included, and collagen having other various forms such as gel form and fiber form may be included.

Figure 5:
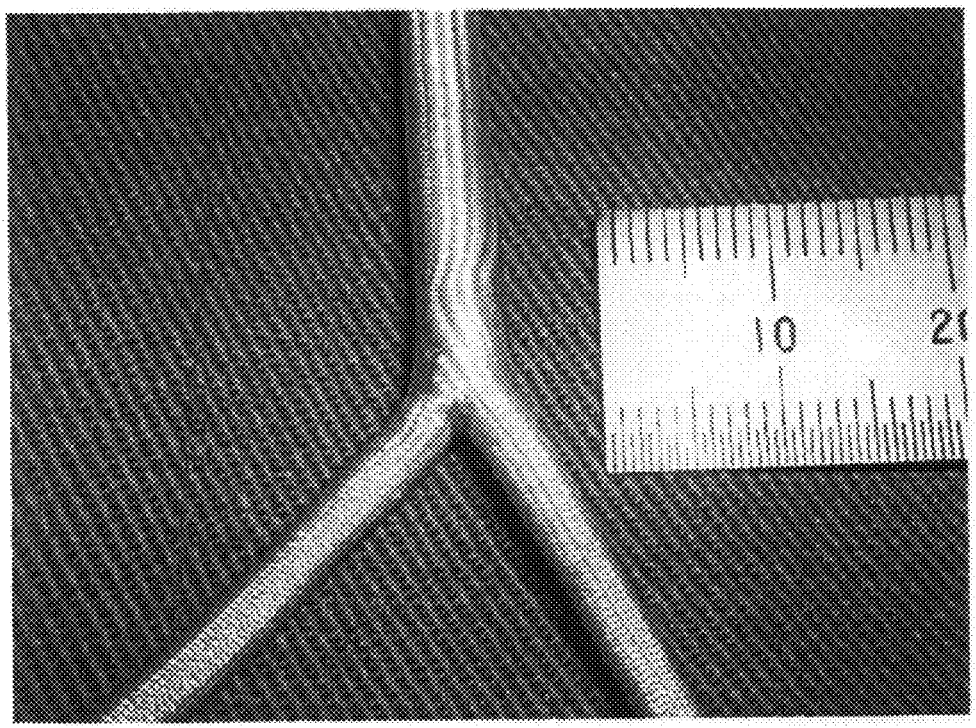
FIG. 5 shows one example of a tubular member for tissue regeneration having a Y-shaped branch.

Furthermore, conventionally, in the neural connection tube, a tubular form having two ends has been known, but the inventors have found that the tube having a branch according to the tissue to be used for and having three or more ends exerts excellent effect. When the tubular or trough-shaped biodegradable support having a branch is used, the tubular or trough-shaped member for tissue regeneration having a branch can be obtained. FIG. 5 shows one example of the tubular member for tissue regeneration having a Y-shaped branch. The number of the branches, the form of the branch (such as Y-shape or T-shape), and shape of the section (such as circle, ellipse, U-shape, or C-shape) (such as overall tubular or trough-shaped form) may be appropriately modified according to the tissue to be applied to. The member for tissue regeneration having such a branch can be used, for example, for reconstruction of branch parts of median nerve of a palm part branching to proper digital nerves in periphery or ischiadic nerve of the part branching to the peroneal nerve and tibial nerve. In particular, the member is useful because the peripheral nerve branching to the periphery can be regenerated by one member for regeneration. It is preferable that the thin film multilocular structure made of collagen according to the present invention is included inside the biodegradable support having a branch, but collagen having other various forms such as gel form or fiber form may be included.

Figure 6:
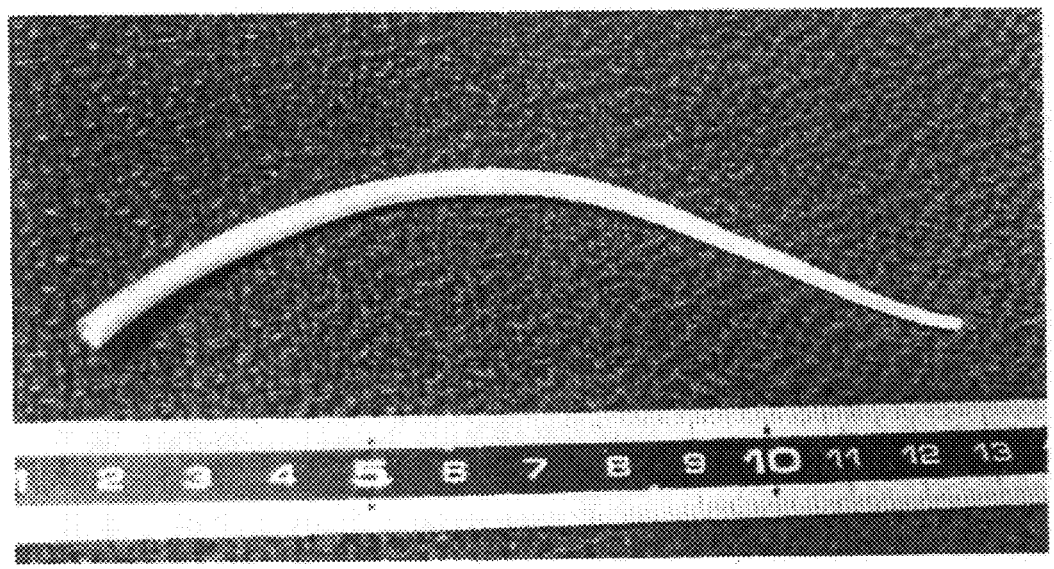
FIG. 6 shows the tapered tubular member for tissue regeneration as one example of the member for tissue regeneration having a difference between the aperture of one end and the aperture of the other end.

Moreover, conventionally, for the nerve connection tube, a tubular tube having a form whose diameter is constant has been known, but the present inventors have found that when there is the aperture difference between the aperture of one end and the aperture of the other end according to the tissue to be used for, the excellent effect is exerted. When the biodegradable support having the aperture difference between the aperture of one end and the aperture of the other end is used, such a member for tissue regeneration can be obtained. FIG. 6 shows a taper-shaped tubular member for tissue regeneration. The member may have the U-shaped or C-shaped section, namely, overall trough-shaped form. For the magnitudes of the apertures of the two ends and the difference of the apertures of both ends, the apertures of the ends may be appropriately adjusted according to the tissue to be applied to and the diameters between the apertures may be continuously changed. The member for tissue regeneration having such aperture difference can be used for, for example, cranial nerve such as facial nerve, brachial plexus, ulnar nerve, radial nerve, median nerve, femur nerve, ischiadic nerve, branches thereof, and further regions in which the peripheral nerve extends from the spinal cord of the central nerve, and in particular, the member is useful for reconstruction of peripheral nerve having an aperture difference between the central part and the peripheral part. It is preferable that the thin film multilocular structure made of collagen according to the present invention is included inside the biodegradable support having aperture difference between the aperture of one end and the aperture of the other end, but collagen having other various forms such as gel form or fiber form may be included.

Furthermore, conventionally, for the nerve connection tube, a plate member is not known, but the present inventors have found that the plate member for tissue regeneration is also possible. By using a plate biodegradable support, such a member for tissue regeneration can be obtained. Such plate member for tissue regeneration can be used, for example, for peroneal nerve, defective part of skin, defective part of dermis, gingival tissue, defective part of soft tissue, and substantially defective part of organ. It is preferable that on a main surface of one side of the biodegradable support, a thin film multilocular structure made of collagen according to the present invention is included, but collagen having other various forms such as gel form or fiber form may be included.

Moreover, within a body, the member for tissue regeneration that is decomposed from the ends of the member for tissue regeneration is preferable because the outer wall around the part in which the tissue is regenerated is sequentially decomposed and therefore nutrient enters into the regenerated tissue from the surround. Furthermore, the member is preferable because the member for tissue regeneration is not required to be removed by a secondary operation.

Figure 7:
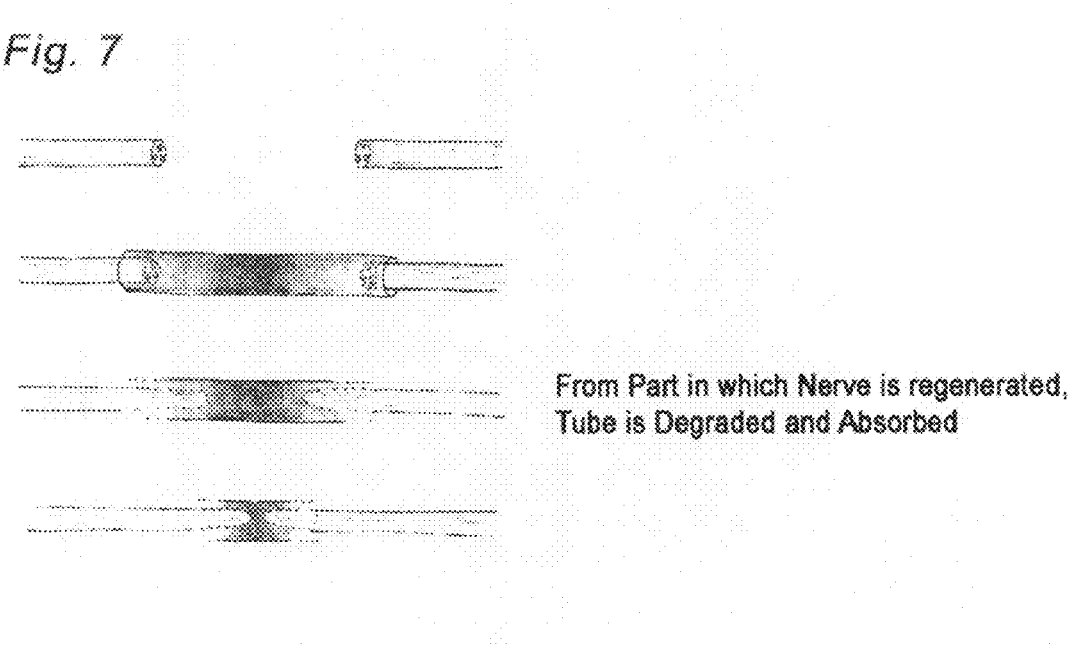
FIG. 7 shows a schematic view showing the tubular member for tissue regeneration that is degraded rapidly in both ends and slowly in the central part, and a schematic illustration of the tissue regeneration by using the member.

FIG. 7 shows a schematic view showing the tubular member for tissue regeneration that is being degraded rapidly in both ends and slowly in the central part, and an schematic illustration of the tissue regeneration by using the member. Nerve tissue is illustrated as the tissue, and there is deficit therein. The gap of the deficit is connected by the tubular member for tissue regeneration. The nerve tissue is regenerated from the both side to the center, and the member for tissue regeneration is decomposed from both ends and absorbed.

Specifically, from both ends of the tubular biodegradable support to the center thereof, for example, the degradation rate of the polymer is sloped (i) by heating or (ii) by irradiation with ultraviolet or radiation, or the degradation rate of the member for tissue regeneration can be controlled (iii) by sloping the extent of crosslink with collagen to be described later, or the like so as to control the degradation rate of the member for tissue regeneration.

It is preferable that the thin film multilocular structure made of collagen according to the present invention is included in the lumen of such a tubular biodegradable support, but collagen having other various forms such as gel form or fiber form may be included.

Furthermore, the present inventors have found it important that for regenerating the long deficit of the tissue, the degradation rate of the entire member for tissue regeneration is controlled by using a biodegradable support in which the structure having the tubular or trough-shaped form is maintained by mixing a raw material which is slowly degraded in vivo with a raw material rapidly degraded in vivo to delay the degradation thereof in vivo.

Here, the "raw material which is rapidly degraded in vivo" is a raw material that is degraded and absorbed generally within three months after implanted in the body, and can include polyglycolic acid (PGA) (its tensile strength decreases by half in two weeks to three weeks), polyglactin 910 (Vicryl), polydioxane (PDS), and PGA+trimethylenecarbonate (TMC), which are conventionally used often as supports.

Moreover, the "raw material which is slowly degraded in vivo" is a raw material that is degraded and absorbed generally in three months or more after implanted in the body, preferably, degraded and absorbed in 6 months to 36 months, and more preferably, degraded and absorbed in 6 months to 24 months, and can include polylactic acid (PLA) and polybutylsuccinate (PBS).

When long deficit is regenerated, it is preferable that the polylactic acid (PLA) fiber to be more slowly degraded in vivo than PGA is mixed in PGA to produce the biodegradable support. There is an example in which PLA is singly used as the support, but the example is not thought to be preferable, and the example in which PGA and PLA are mixed and used as the support is not known. When PLA is mixed, the degradation rate of the support becomes inactive, and the biodegradable support in which the structure having a hollow interior (such as lumen structure in the tubular shape) can be maintained in vivo for a long period can be obtained.

Figure 8:
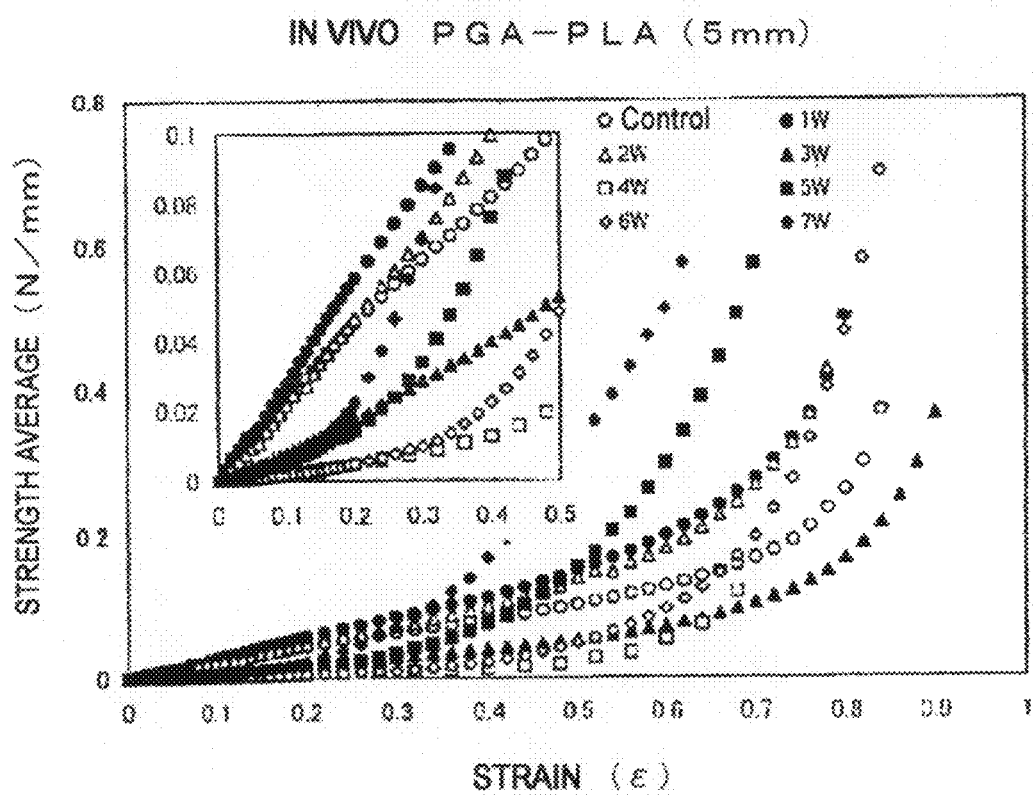
FIG. 8 shows strength (average) with respect to strain of PGA-PLA member for tissue regeneration (including 50% of PLA).
Figure 9:
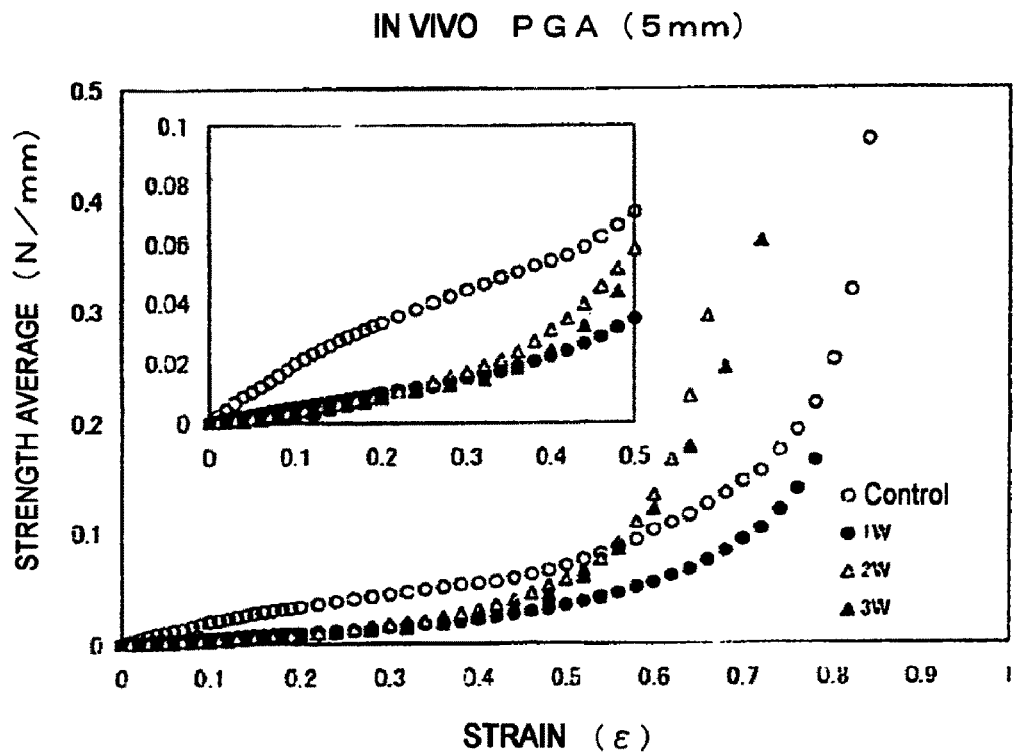
FIG. 9 shows strength (average) with respect to strain of PGA member for tissue regeneration.
Figure 10:
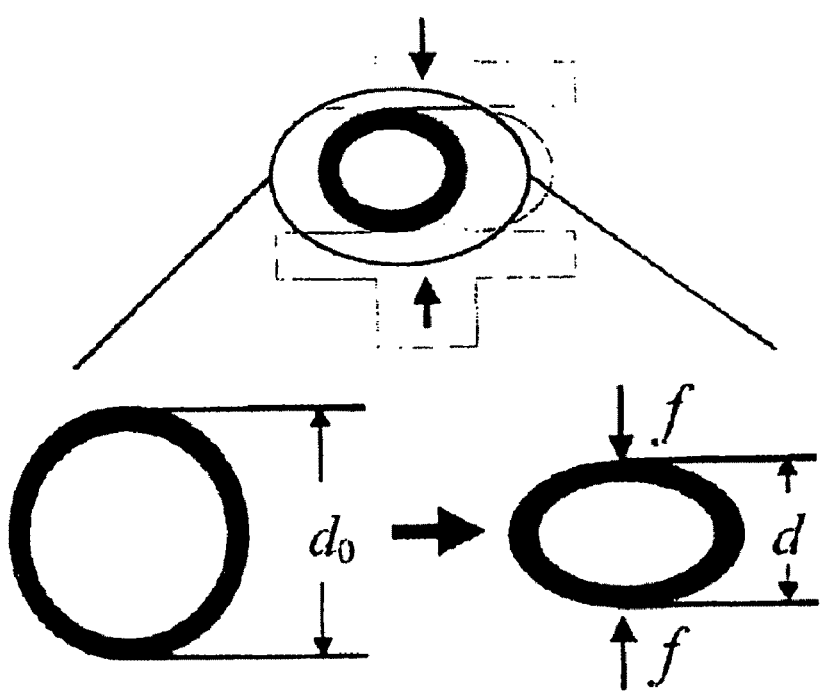
FIG. 10 is a schematic view for explaining the strain and the strength displayed in FIGS. 8 and 9.

FIG. 8 shows strength (average) with respect to strain of the tube made of PGA and PLA for tissue regeneration (including 50% of PLA). FIG. 9 shows strength (average) with respect to strain of the general tube made of PGA for tissue regeneration. FIG. 10 is a schematic view for explaining the strain and the strength described in FIGS. 8 and 9. It is understood that in a general PGA tube, after implanting the tube in the body, lowering of mechanical strength is immediately caused, but the strength is improved by combining PLA and PGA. In FIGS. 8 and 9, scheme ($d_o$–d/$d_o$) is plotted in the horizontal axis, and applied force (f of length of unit) is plotted in the longitudinal axis, and it can be understood that FIG. 8 in which 50% of PLA is mixed has higher strength than that of FIG. 9 when the same strain is added. That is, it has been found that by mixing 50% of PLA fiber, the mechanical strength of the tube is improved and the lowering of strength after implanting the tube in vivo is inactive. Therefore, it is preferable to use a support in which PGA and PLA are combined. It is preferable that the mixing ratio of PGA and PLA (PGA/PLA) (fiber bundle number ratio) is 10 to 90/90 to 10, and the mixing ratio of 50/50 is particularly preferable.

As such a combination, additionally, for example, PGA and PBS and so forth can be exemplified. It is preferable that the thin film multilocular structure made of collagen according to the present invention is included inside such a biodegradable support, but collagen having other various forms such as gel form or fiber form may be included.

For regenerating a long deficit of tissue, it is more preferable to use the biodegradable support having a tubular or trough-shaped form in which the degradation rate of the biodegradable support is controlled such that the decomposition rate of the ends is higher than that of the central portion in vivo and in which the structure having a hollow interior is maintained by mixing a raw material which is slowly degraded in vivo with a raw material which is rapidly degraded in vivo to delay the degradation in vivo. Such a biodegradable support can be produced by combining PLA with PGA to produce, for example, a tube and then using the above-described methods (i) to (iii) or the like for sloping the degradation rate.

It is more preferable that the thin film multilocular structure made of collagen according to the present invention is included inside such a biodegradable support. Collagen having other various forms such as gel form or fiber form may be included.

The thin film multilocular structure made of collagen according to the present invention can be produced without limitation by the production method as long as the structure to be desired can be obtained, and, for example, the structure can be produced by freeze-drying a collagen solution. More specially, for example, the aqueous solution of atelocollagen is frozen using a deep freezer, and then, dried by freeze-drier, and subjected to thermal cross-linking treatment under vacuum conditions. It is preferable that the concentration of a dilute hydrochloric acid solution of atelocollagen is 0.5 to 3.5% by weight, and 1.0 to 3.0% by weight is more preferable, and 1.0 to 2.0% by weight is particularly preferable. It is preferable that the concentration of the dilute hydrochloric acid is 0.0001 to 0.01 N, and 0.001 N is particularly preferable. It is preferable that pH of the dilute hydrochloric acid is 2 to 4, and 3 is particularly preferable. It is preferable that the freeze temperature is −70 to −100° C., and −80 to −90° C. is particularly preferable. It is preferable that freeze-drying is performed for 24 hours under a reduced pressure of 5.0 Pa or less at −80° C. to −90° C. It is preferable that the thermal cross-linking treatment is performed for 6 to 48 hours at 100 to 150° C. under a reduced pressure of 1 Torr or less, and it is more preferable to perform the treatment for 12 to 48 hours at 120 to 145° C., and it is particularly preferable to perform the treatment for 48 hours at 140° C. In particular, for nerve tissue, such a thin film multilocular structure can suitably used.

The member for tissue regeneration including a biodegradable support supporting the thin film multilocular structure made of collagen according to the present invention can be produced without being particularly limited by the production method as long as the desired member for tissue regeneration can be obtained, and for example, the member can be produced by the following method. A collagen solution is attached to the biodegradable support, and then, the collagen solution is freeze-dried, and thereby, the member can be produced. More specifically, for example, when the support has a tubular shape, a tube having an appropriate size is immersed in 70% ethanol for 24 hours, and then, the ethanol is completely dried, and 1.0 to 3.0% by weight of the collagen dilute hydrochloric acid solution (0.001 N) (pH 3.0) is applied to the biodegradable support surface and air-dried. And, the application and air-drying process are repeated at 20 times to form collagen coating on the support surface. The member is preliminarily cooled to −85° C. in a freezer, and then, 1.0 to 3.0% by weight of the collagen hydrochloric acid solution (pH 3.0) at +4° C. is filled inside the member so as not to generate a gap by a slim syringe, and immediately, the member is put in a deep freezer, and cooled to −85° C. to be frozen. The member is put in a freeze-drier and dried for one day (for 24 hours) at −80° C. to evaporate the moisture. Then, under vacuum conditions (1 Torr or less), thermal dehydration cross-linking treatment is performed for 24 to 48 hours at 120° C. to 140° C., and thereby, the member for tissue regeneration can be obtained.

The tubular biodegradable support can be produced by a conventionally known method, for example, forming a tubular wall around a tubular core material.

The tubular biodegradable support having a branch can be produced by forming a tubular wall around the core material having a branch structure (the outer diameter of each of the branches is 5 mm). Hereinafter, the production will be explained in detail.

A tube is made by using a core material having a branch by using a braiding apparatus. As the biodegradable fiber to be used, PGA fiber can be used. As the PGA fiber, for example, a PGA fiber obtained by bundling up five PGA multi-filaments each of which is obtained by bundling up 28 filaments each having a single-yarn fineness of 2.55 dtex/F can be used. For example, by using a braiding apparatus of 48 bobbins, formation of the tube is started from one end. When the braiding apparatus reaches the branch part of the core material, the branch of the branching core material on which a tube is formed later is diverted to the outside through a gap of the fibers, and thereby, the braiding apparatus passes through the branch part and a tube can be formed on one branch of a branching core material. After the tube is folded to the second end, a tube is repeatedly formed and superposed from the one end. When the braiding apparatus reaches the branching part again, the branching branch around which the tube has been formed previously is diverted to the outside through a gap of the fibers. A tube is formed on the other branch as a core around which no tube is formed previously. By forming the tube to the third end, the tubular support having an integrated branching structure can be obtained. For the core material of the branching structure, a soft raw material is required to be used because the branching branch has to be passed through a gap of fibers of the tubular wall.

As a producing method other than this, the following producing method can be exemplified. After the tube is formed from one end to the branching part by a braiding apparatus, the tubular wall is produced to the second end on one core material of the branching branches by using the half of the PGA fibers of the braiding apparatus. Then, by using the residual half of the PGA fibers, the tubular wall is produced to the third end on the other core material of the branching part.

Moreover, plate-shaped biodegradable support can be produced, for example, by plain-weaving the raw material of the biodegradable support or by producing a tubular material having a large diameter and incising the material in the longitudinal direction and then expanding the material.

The biodegradable support having a trough-shaped form whose section has a U-shape or C-shape can be produced by incising the tubular wall of the tubular support in the longitudinal direction or by excising a part of the tubular wall of the tubular support.

The biodegradable support having the aperture difference between the aperture of one end and the aperture of the other end can be produced, for example, by preliminarily producing a core material having the aperture difference between the apertures of both ends (taper core material) and forming a tube by using the material as the core by, for example, a braiding apparatus.

The biodegradable support having a tubular or trough-shaped form whose degradation rate is higher as being nearer to the ends from the central portion in vivo can be produced the above-described method.

Moreover, the biodegradable support in which the form has a hollow interior by mixing a raw material which is slowly degraded in vivo with a raw material rapidly degraded in vivo to delay the degradation thereof in vivo can be produced by forming the tubular wall by using such a raw material as described previously.

The biodegradable support in which a plurality of forms are combined can be produced by appropriately combining the above-described producing methods.

The member for tissue regeneration including the above-described thin film multilocular structure made of collagen can be produced by producing "the thin film multilocular structure" of collagen in the lumen by filling and freeze-drying a collagen solution in the various biodegradable supports.

The member for tissue regeneration including collagen having various forms such as gel form or fiber form may be produced by filling the various biodegradable supports with the sponge-formed collagen or fiber-formed collagen by using a conventionally known method.

The aspects and embodiments of the present invention described above can be appropriately combined when possible.

EXAMPLES

Example 1

Production of Thin Film Multilocular Structure Made of Collagen 1 to 3% by weight of a dilute hydrochloric acid (0.001 N) solution (pH=about 3.0) of atelocollagen (NMP collagen PSN (trade name) manufactured by Nippon Meat Packers, Inc. derived from pig dermis) was produced and poured into a frame, and then, freeze-dried in a deep freezer at −80° C. to −86° C. This was dried for 24 to 48 hours at −80° C. in a freeze-drier to evaporate the moisture, and thereby, the thin film multilocular structure was obtained. The cross-linking treatment by heating was performed for 24 hours at 140° C. under vacuum conditions. When the structure was observed under a scanning electron microscope of a 20 kV acceleration voltage, a thin film multilocular structure was observed. This is shown in FIGS. 1(a) to 1(c).

Moreover, by the same method, a further thin film multilocular structure was obtained. When this was observed by a scanning electron microscope using a 18 kV acceleration voltage, the thin film multilocular structure shown in FIGS. 1(d) and 1(e) was observed.

Example 2

Production of Member for Tissue Regeneration in which Thin Film Multilocular Structure Made of Collagen is Included Inside Tubular Biodegradable Support The PGA tube produced by a known method was cut into appropriate length. The cut tube was immersed in 70% ethanol for 24 hours. The PGA tube was taken out of 70% ethanol and then dried completely. The outside of the PGA tube was coated by about 20 times by using 1 to 3% by weight of a dilute hydrochloric acid (0.001 N) solution (pH=about 3.0) of atelocollagen (NMP collagen PSN (trade name) manufactured by Nippon Meat Packers, Inc. derived from pig dermis), and then dried. By removing the core from the PGA tube, the tubular support was obtained. By a syringe, 1 to 3% by weight of a dilute hydrochloric acid (0.001 N) solution (pH=about 3.0) of atelocollagen (NMP collagen PSN (trade name) manufactured by Nippon Meat Packers, Inc. derived from pig dermis) was packed into the tubular support. This was frozen in a deep freezer at −80° C. to −86° C. This was dried for 24 to 48 hours at −80° C. by the freeze-drier. The cross-linking treatment by heating is performed for 24 hours at 140° C. under vacuum of 1 Torr or less, and thereby, the member for tissue regeneration was obtained. When the member was observed by the scanning electron microscope of a 20-kV acceleration voltage, the thin film multilocular structure was observed inside the tubular support. This is shown in FIGS. 2(a) and 2(b).

When the member for tissue regeneration was used for regenerating peroneal nerve of dog, not only pathologic-histologically but also electrophysiologically preferable recovery of the nerve function was observed.

Example 3

A PGA tube, namely, a tubular biodegradable support was produced by using a braid-producing apparatus, and the member for tissue regeneration (referred to as "tube A1") in which the thin film multilocular structure as the new structure made of collagen inside the support was formed in the same manner as Example 2 was produced (diameter: 2 mm, length: 10 mm). On the other hand, as the experiment control, a PGA tube (referred to as "tube B1") in which Microfibril collagen was filled which is commercially available as a medical device (Integran (trade name) manufactured by Koken Co., Ltd.) was used (diameter: 2 mm, length: 10 mm).

5 mm nerve defective part of right ischiadic nerve of Wistar rat (n=2) was reconstructed by using the tube A1. As a control, 5 mm defective part of left ischiadic nerve thereof was reconstructed by using the tube B1.

After one month, the Wistear rats were put down, and diameter of axial filament and thickness of myelin sheath in the distal end of the nerve reconstruction part and the number of myelinated nerve axons were measured. In the tube A1, the measurements were 1.4±0.3 μm/0.4±0.08 μm/60±25 count per 100×100 μm$^2$, respectively, and in the tube B1, they were 1.0±0.4 μm/0.2±0.10 μm/92±31 count per 100×100 μm$^2$, respectively, and therefore, better regeneration was significantly observed in the tube A1.

Example 4

A PGA tube, namely, a tubular biodegradable support was produced by using a braid-producing apparatus, and the member for tissue regeneration (referred to as "tube A2") in which the thin film multilocular structure as the new structure made of collagen inside the support was formed in the same manner as Example 2 was produced (diameter: 2 mm, length: 10 mm). On the other hand, as the experimental control, a PGA tube (referred to as "tube C1") in which collagen fibers having a diameter of 400 μm were bundled and filled was produced (diameter: 2 mm, length: 10 mm).

5 mm nerve defective part of right ischiadic nerve of Wistar rat (n=2) was reconstructed by using the tube A2. As the control, 5 mm defective part of left ischiadic nerve thereof was reconstructed by using the tube C1.

After one month, the Wistear rats were put down, and the diameter of the axial filament and the thickness of the myelin sheath in the distal end of the nerve reconstruction part and the number of myelinated nerve axons were measured. In the tube A2, the measurement were 1.3±0.5 μm/0.3±0.07 μm/61±22 count per 100×100 μm$^2$, respectively, and in the tube C1, they were 0.9±0.3 μm/0.2±0.05 μm/103±30 count per 100×100 μm$^2$, respectively, and therefore, better regeneration was significantly observed in the tube A2.

Example 5

Production of Member for Tissue Regeneration in which Thin Film Multilocular Structure Made of Collagen is Included Inside Biodegradable Support Having Trough-Shaped Form Whose Section has U-Shape By using PGA fiber (The PGA fiber was obtained by bundling up two PGA multi-filaments each of which was obtained by bundling up 28 filaments each having a single-yarn fineness of 2.59 dtex/F), a tube of PGA having an inner diameter of 2 mm (length=10 m) was obtained by using a braid-producing apparatus of 48 bobbins (reels) so that Teflon (Registered trademark) tube having an outer diameter of 2 mm served as the core material. After cutting this into a length of 5 cm together with the core material, the treatment in which 1.0% by weight of collagen dilute hydrochloric acid solution (0.001 N, pH about 3.0) was coated thereon and the tube was dried was repeated by 20 times, and thereby the tubular support was obtained. Then, the core material was pulled and removed, and a collagen solution was filled inside the tubular support, and freeze-dried, and thermally cross-linked to produce the tubular member for tissue regeneration including collagen having a thin film multilocular structure inside. ⅓ of the outer wall of the member for tissue regeneration was excited by using a sharp scissor for microsurgery under a stereomicroscope to produce the U-shaped member for tissue regeneration. This was shown in FIGS. 3 and 4. In FIG. 4, the member for tissue regeneration including the biodegradable support having overall a trough shape was implanted in a 1 cm defective part of a femur ischiadic nerve of rat having a body weight of 300 g, and the operation time required for implanting was about 10 minutes. By contrast, when the member for tissue regeneration including the tubular biodegradable support having the same size is used to perform the connection, the required time is generally about 20 minutes, and therefore, the operation time could be saved by about 50%.

Here, by excising the outer wall of the tubular member for tissue regeneration, the member for tissue regeneration having a trough-shaped form was produced, but the member for tissue regeneration having trough-shaped form may be produced by forming a thin film multilocular structure made of collagen inside the biodegradable support having the trough-shaped form.

Example 6

Production of Tubular Biodegradable Support Having Y-Shaped Branch and Member for Tissue Regeneration Including the Support First, by using a thermoplastic polyolefin synthetic polymer that is soft at room temperature, a Y-shaped core material was molded. The outer diameter of each of the branches of the Y-shape was 5 mm and the length thereof was 10 cm. By using this as the core material, the Y-shaped tube was produced from PGA fiber (The PGA fiber obtained by bundling up five PGA multi-filaments each of which was obtained by bundling up 28 filaments each having a single-yarn fineness of 2.59 dtex/F was reeled) by a braid apparatus at 48 punches. This process will be explained further specifically. A tube was formed on the above-described core material from one end under the Y shape. After one core branch was pulled outside the tube in reaching the branching part of the Y shape, the tube was sequentially produced to the second end so that the residual branch serves as the core material. Thereby, the PGA tube having a shape in which a naked core material projected as a branch in the center was produced. In the same manner as the previous production, from the one end under the Y shape, the PGA tube was produced again so that the tube previously produced itself serves as the core. After the production to the branch part, the branching branch (core material) having the one end around which PGA was formed was pulled to the outside. By forming the tube to the third end so that the branching branch on which the tube is not previously formed serves as the core material, a seamless integrated Y-shaped tube was produced.

To the obtained Y-shaped biodegradable support, a collagen solution is attached and freeze-dried, and thereby, the "thin film multilocular structure" of collagen is made and contained, and thereby, the tubular member for tissue regeneration branching in a Y shape including the thin film multilocular structure made of collagen can be produced.

Example 7

Experiment of Introduction of Neural Cell into Tubular Member for Tissue Regeneration Having Y-Shaped Branch A Y-shaped PGA tube, namely, a Y-shaped biodegradable support was produced by using a braid-producing apparatus, and the Y-shaped member for tissue regeneration inside which the thin film multilocular structure was formed in the same method as Example 2 as the new structure made of collagen was produced. The diameter of each of the branches was 4 mm and the length thereof was 3 cm. The angles of the three corners formed by the branches were all 60°.

The Y-shaped member for tissue regeneration was put in a culture petri dish and immersed in the neural cell culture medium (MB-X9501D manufactured by Dainippon Sumitomo Pharma Co., Ltd.), and neural cells (MB-X032D manufactured by Dainippon Sumitomo Pharma Co., Ltd.) of two embryos was divided into three and injected into the three openings of the Y-shaped member. After culturing this in an incubator for two weeks, the inside of the Y-shaped member for tissue regeneration was observed. It was confirmed that the neural cells pervaded the entire part of the thin film multilocular structure made of collagen filled inside the Y-shaped member for tissue regeneration and had proliferated and progressed. It is thought that this is because the member for tissue regeneration having the branch structure has high affinity with the cells derived from nerve as the nerve guide tube.

Example 8

Production of Tubular Biodegradable Support Having Difference Between Aperture of One End and Aperture of the Other End and Member for Tissue Regeneration Including the Support First, by heating and processing a thermoplastic polyolefin synthetic polymer material having plasticity at room temperature, 30 core materials each having a length of 10 cm, an outer diameter of one end of 3 mm, an outer diameter of the other end of 1 mm, and a tapering shape whose outer diameter decreased linearly from the one end to the other end were produced. Next, a long core material was produced connecting the 30 core materials so that the slim ends faced one another and so that the thick ends faced one another. By using this long core material, the tube of PGA fiber was produced by a braid-producing apparatus and cut to produce 30 biodegradable supports each having the aperture difference between both ends. In producing the tube of the PGA fiber, it was devised that by setting the tube-folding rate to be slow in the part having the thick aperture and the tube-folding rate to be more rapid as the core material became more slim, mechanical strength of the tube did not become weak in the thick side, and that is, the entire strength was made to be uniform.

To the obtained tubular biodegradable support having the aperture difference, a collagen solution was attached and freeze-dried, and thereby, the "thin film multilocular structure" of collagen was made to be contained, and thereby, tubular member for tissue regeneration having the aperture difference including the thin film multilocular structure made of collagen can be produced.

Example 9

Tubular Biodegradable Support Whose Degradation Rate is Controlled Such that Decomposition Rate of Ends is Higher than that of Central Portion In Vivo and In Vivo Degradation Property Thereof By using a braid-producing apparatus and by using a polylactic acid (PLA) fiber, which is slowly degraded, a tube having a diameter of 5 mm and a length of 4 cm was produced. Next, in the state of covering the right half of the tube with a cold insulator, hot air was applied to the left half of the tube for 30 minutes by using a drier at 1,200 W and 105° C. Furthermore, after covering the left half of the tube with a cold insulator, hot air was applied to the right end of the tube in the same manner. Thereby, a tube that was more exposed to the high temperature as being nearer to both ends of the tube was produced. When the tube was implanted under a skin of a back of a rat, it was confirmed that the degradation was initiated in vivo from the ends of the tube from the third week after insertion. By the heating treatment, both ends were degraded and absorbed in about one month and the central portion thereof was degraded and absorbed in two to three months. That is, it was confirmed that the tube, namely, the biodegradable support whose degradation rate in vivo is higher as being nearer to both ends can be produced.

Example 10

Production of Biodegradable Support in which Tubular Structure is Maintained by Mixing Raw Material which is Slowly Degraded In Vivo with Raw Material which is Rapidly Degraded In Vivo to Delay Degradation Thereof in Vivo, and Member for Tissue Regeneration Including the Support The PGA-PLA tube was produced by producing a tube in which the polylactic acid (PLA) fiber which is slowly degraded was mixed with polyglycolic acid (PGA) (PGA/PLA=50/50 (fiber bundle ratio)) by using a braid-producing apparatus. To the outside of this tube, 1% by weight of a collagen aqueous solution was applied and dried. This process was repeated by 20 times to obtain the above biodegradable support. Then, inside the tubular PGA-PLA biodegradable support, 1% by weight of a collagen aqueous solution is filled, and immediately freeze-dried to form the thin film multilocular collagen inside. Then, thermal cross-linking treatment was performed for 24 hours at 140° C., and thereby, the tubular member for tissue regeneration containing 1% by weight of the thin film multilocular collagen inside and having a diameter of 5 mm and a length of 40 mm (hereinafter, also referred to as "PGA-PLA member for tissue regeneration) was produced.

40 mm nerve defective part of the right peroneal nerve of beagle dog (n=12) was reconstructed by using the PGA-PLA member for tissue regeneration. As a control, 40 mm nerve defective part of the right peroneal nerve of beagle dog (n=12) was reconstructed by using a tubular member for tissue regeneration (hereinafter, this is also "PGA member for tissue regeneration") produced in the same method except that no PLA was mixed instead of the PGA-PLA member for tissue regeneration.

In the PGA member for tissue regeneration, the tubular structure could not be maintained in two weeks after the reconstruction and was degraded and absorbed mostly in one month, and by contrast, in the PGA-PLA member for tissue regeneration, there was almost no change of the lumen structure even if two months elapsed, and the lumen structure had been maintained even in the tissue evaluation after six months after the reconstruction.

The mechanical property of the PGA-PLA member for tissue regeneration was shown in FIG. 8. The mechanical property was measured by using Tensilon®-250 (trade name) manufactured by ORIENTEC Co., Ltd. under the condition of axial pressurization at 37° C. in a normal saline pH 6.4 at a crosshead rate of 1 mm/min. The mechanical property of the PGA member for tissue regeneration was measured in the same manner and is shown in FIG. 9. Considering using the member for a long defective part by delaying the degradation rate, it is preferable that the member has a larger mechanical strength. When FIGS. 8 and 9 are compared as described above, it is understood that the PGA-PLA member for tissue regeneration has a larger strength in the case of adding the same strain and therefore can bear the use of a longer period.

For the obtained biodegradable support, members for tissue regeneration including collagen having various forms such as gel form or fiber form can be further produced.

Furthermore, the present inventors have performed intensive studies, and as a result, have found that when the peripheral nerve damaged site causing pain is reconstructed by using the member for tissue regeneration including the thin film multilocular structure made of collagen according to the present invention, the pain disappears after the operation.

That is, conventionally, it has been known that the nerve connection tube has an effect with respect to perception loss or motor paralysis of the nerve defective site, but the present inventors have found that by using the member for tissue regeneration including the thin film multilocular structure made of collagen according to the present invention in the nerve defective site causing the pain, the pain disappears and further the normal sense recovers.

Example 11

Improvement of Pain by Member for Tissue Regeneration Including Thin Film Multilocular Structure Made of Collagen A man of forty-two years incompletely mutilated his left first finger with an electrical saw in a work accidentally six months previously and underwent a reattachment operation. However, the re-attached left first finger caused intensive pain to make the left hand unusable and to make his daily life inconvenient. Accordingly, the digital nerve damaged site was excised and a reconstruction operation was performed in which the site was cross-linked with the member for tissue regeneration including the thin film multilocular structure made of collagen according to the present invention, and therefore, the pain disappeared after the operation and it became possible to use the left hand, and in the sixth month after then, the sense of the left first finger completely recovered.

Example 12

Improvement 2 of Pain by Member for Tissue Regeneration Including Thin Film Multilocular Structure Made of Collagen A man of thirty-seven years dropped from a height of 2 m and the right distal radius was complexly fractured, and he was subjected to an internal fixation and the external fixation as the initial treatment. After the initial treatment, intensive pain expanded from the wrist to the right upper limb, and the right upper limb became a disuse limb. The bone atrophy of the right hand was observed by X-ray photograph, and was diagnosed as complex regional pain syndrome (CRPS—type II). The patient lost 12 kg in weight in four months because of the intensive pain. Conventionally, such complex regional pain syndrome has been supposed to be difficult to be surgically treated. The present inventors confirmed that there was a disorder in one cutaneous branch of the right radial nerve, and the surrounding nerve was delaminated, and then, the disorder site of this nerve was excised by operation and was reconstructed through cross-linking with the member for tissue regeneration including the thin film multilocular structure made of collagen. Accordingly, the pain before the operation of the patient disappeared immediately after awakening from the anesthesia. In the X-ray photograph of 12 months after the operation, it was confirmed that the bone atrophy was reclaimed and the cutaneous temperature returned to be normal. The motor function of the right hand, which had become a disused limb, recovered after the operation, and the patient became capable of doing up and undoing the buttons of shirts with his hand on the damaged side and returned to a normal life.

INDUSTRIAL APPLICABILITY

The thin film multilocular structure made of collagen according to the present invention has a new structure different from colloidal form, gel form, and fiber form. Therefore, when the new structure made of collagen according to the present invention is used for the member for tissue regeneration, promotion of regeneration, shortening of treatment period, functional recovery, or the like of bodily tissue such as nerve tissue, subdermal tissue, submucosal tissue, membranous tissue, fat tissue, muscle tissue, skin tissue, and gingival tissue can be improved.

Furthermore, when the above-described member for tissue regeneration further includes the biodegradable support, the tissue to be regenerated can be further protected.

When the member for tissue regeneration according to the present invention comprises the above thin film multilocular structure inside of the tubular biodegradable support, a long and thin fibrous tissue can be regenerated more advantageously.

As described above, the member for tissue regeneration according to the present invention is extremely useful for regenerating bodily tissues, and furthermore, when the patient has neuropathic pain, the member has an effect on the disappearance of the pain, and so forth, and therefore, the member is extremely useful medically.

The invention claimed is:

1. A thin film multilocular structure made of collagen, wherein the multilocular structure comprises a plurality of loculi or chambers between a plurality of films, and which is obtained by freezing a diluted hydrochloric acid solution of collagen at a freeze temperature of −70 to −100° C. and then freeze-drying the same.

2. A member for tissue regeneration containing the thin-film multilocular structure according to claim 1.

3. The member for tissue regeneration according to claim 2, wherein the member includes a biodegradable support.

4. The member for tissue regeneration according to claim 3, wherein said thin film multilocular structure is inside a tubular biodegradable support.

5. The member for tissue regeneration according to claim 4, wherein the biodegradable support has a branch.

6. The member for tissue regeneration according to claim 4, wherein there is a difference in aperatures between an aperture at one end of the biodegradable support and an aperture at the other end of the biodegradable support.

7. The member for tissue regeneration according to claim 4, wherein degradation rate of the biodegradable support in vivo is changed such that the decomposition rate of the ends is higher than that of the central portion.

8. The member for tissue regeneration according to claim 4, wherein a structure having a hollow interior is maintained by mixing a raw material degraded slowly in vivo with a raw material degraded rapidly in vivo to delay the degradation thereof in vivo.

9. The member for tissue regeneration according to claim 4, wherein the member for tissue regeneration is used as a member for nerve tissue regeneration.

10. The member for tissue regeneration according to claim 3, wherein said thin film multilocular structure is inside a biodegradable support having a trough-shaped form whose section has a U-shape or C-shape.

11. The member for tissue regeneration according to claim 10, wherein the biodegradable support has a branch.

12. The member for tissue regeneration according to claim 10, wherein the member for tissue regeneration is used as a member for nerve tissue regeneration.

13. The member for tissue regeneration according to claim 3, wherein the member for tissue regeneration is used as a member for nerve tissue regeneration.

14. The member for tissue regeneration according to claim 2, wherein the member for tissue regeneration is used as a member for nerve tissue regeneration.

* * * * *